US012715683B2

(12) United States Patent
Teles et al.

(10) Patent No.: US 12,715,683 B2
(45) Date of Patent: Aug. 25, 2026

(54) CONTAINER AND PROCESS FOR THE STORAGE OF A SATURATED ALIPHATIC C6-C12 CARBOXYLIC ACID

(71) Applicant: BASF SE, Ludwigshafen am Rhein (DE)

(72) Inventors: Joaquim Henrique Teles, Ludwigshafen am Rhein (DE); Jessica Nadine Hamann, Ludwigshafen am Rhein (DE); Shelue Liang, Ludwigshafen am Rhein (DE); Stefan Rittinger, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 111 days.

(21) Appl. No.: 18/032,193

(22) PCT Filed: Oct. 12, 2021

(86) PCT No.: PCT/EP2021/078106

§ 371 (c)(1),
(2) Date: Apr. 17, 2023

(87) PCT Pub. No.: WO2022/084094

PCT Pub. Date: Apr. 28, 2022

(65) Prior Publication Data

US 2023/0391542 A1 Dec. 7, 2023

(30) Foreign Application Priority Data

Oct. 22, 2020 (EP) .................................... 20203292

(51) Int. Cl.

*B65D 85/84* (2006.01)
*B65D 81/20* (2006.01)
*C07C 51/50* (2006.01)
*C07C 53/126* (2006.01)

(52) U.S. Cl.

CPC ............ *B65D 85/84* (2013.01); *B65D 81/20* (2013.01); *C07C 51/50* (2013.01); *C07C 53/126* (2013.01)

(58) Field of Classification Search

CPC ....... C07C 51/50; C07C 53/126; B65D 85/84; B65D 85/20

See application file for complete search history.

(56) References Cited

U.S. PATENT DOCUMENTS 3,959,321 A * 5/1976 McKenna, III ....... C11B 5/0071 562/606

FOREIGN PATENT DOCUMENTS

| | | | | |
|---|---|---|---|---|
| CN | 102245589 | A | 11/2011 | |
| CN | 203529201 | U * | 4/2014 | ............ B65D 81/20 |
| EP | 0106445 | A1 | 4/1984 | |
| WO | 2004/108648 | A1 | 12/2004 | |
| WO | 2010/069893 | A1 | 6/2010 | |
| WO | 2017/145106 | A1 | 8/2017 | |

OTHER PUBLICATIONS

Schillmoller, C.M., et al., Alloy selection for srevic3e in organic acids, , Nickel Institute, Aug. 2020, Second Edition, 12 pages (Year: 2020).*

Kubitschke et al., Carboxylic acids, Aliphatic, Ullmann's Encyclopedia of Industrial Chemistry, pp. 1-18 (Year: 2014).*

Hamann, et al., Unpublished EP Application No. 20191855.4, filed on Aug. 20, 2020, titled "Process for the preparation of C6 12 saturated aliphatic carboxylic acids", 38 pages.

International Search Report and Written Opinion received for PCT Patent Application No. PCT/EP2021/078106, mailed on Feb. 3, 2022, 11 pages.

Kubitschke et al., "Carboxylic Acids, Aliphatic," Ullmann's Encyclopedia of Industrial Chemistry, May 30, 2014, pp. 1-18.

Nigel Allen, "Hazards of high flash point liquids in relation to the ATEX 137 Directive", Hazards XXI, Symposium Series No. 155, 2009, pp. 271-276. URL—https://www.icheme.org/media/9668/xxi-paper-040.pdf.

Uhl, et al., "Peroxy Compounds, Organic", Ullmann's Encyclopedia of Industrial Chemistry, Feb. 1, 2018, pp. 1-45.

* cited by examiner

*Primary Examiner* — Yate' K Cutliff

(74) *Attorney, Agent, or Firm* — Faegre Drinker Biddle & Reath LLP

(57) ABSTRACT

A container and a process for the degradation stable storage and transport of a liquid comprising a saturated aliphatic $C_{6-12}$ carboxylic acid in which the liquid is covered with an oxygen free or at least heavily oxygen depleted inert gas phase atmosphere above the liquid.

13 Claims, No Drawings

CONTAINER AND PROCESS FOR THE STORAGE OF A SATURATED ALIPHATIC C6-C12 CARBOXYLIC ACID

CROSS-REFERENCE TO RELATED APPLICATIONS

This application is a National stage application (under 35 U.S.C. § 371) of PCT/EP2021/078106, filed Oct. 12, 2021, which claims benefit of European Application No. 20203292.6, filed Oct. 22, 2020, both of which are incorporated herein by reference in their entirety.

The present invention relates to a container with an inner volume of 0.05 to 10000 $m^3$ for the storage and transport of a liquid comprising a saturated aliphatic $C_{6-12}$ carboxylic acid or a mixture thereof, whereas the liquid has a saturated aliphatic $C_{6-12}$ carboxylic acid content of 99 to 100 wt.-%, in which the liquid occupies 1 to 99% of the inner volume of the container and a gas phase is present above the liquid.

Furthermore, the present invention also relates to a process for the storage and transport of such a liquid in such a container, in which the liquid is filled into the container occupying 1 to 99% of the inner volume of the container, being covered by a gas phase, and being kept therein for more than 1 hour.

Saturated aliphatic carboxylic acids are important intermediates globally with a wide range of applications. They can be used as such, but are typically further processed to metal salts, esters, amides, anhydrides, acid chlorides, and other derivatives. Overall, they are important intermediates for the production of a wide variety of compounds such as metal salts and metal soaps, flavors, fragrances, pharmaceutical and agrochemical ingredients, cosmetic ingredients, plasticizers, paints, coating additives, coolants, lubricants or catalysts for polymer processing. A very important representative of a $C_{6-12}$ saturated aliphatic carboxylic acid is 2-ethylhexanoic acid. It is mainly used in the form of its derivatives as for example its metal salts or esters for their use as drying agents and thickeners for alkyd resins and paints, as catalysts in polyurethane foam manufacturing, as PVC stabilizers and/or plasticizers, or as anti-wear agents and corrosion inhibitors for lubricants. Esters of $C_{6-12}$ saturated aliphatic carboxylic acids such as of n-heptanoic acid, n-octanoic acid, 2-ethylhexanoic acid, n-nonanoic acid or 3,5,5-trimethylhexanoic acid are also often used as lubricants.

A widely used and important method for the production of saturated aliphatic $C_{6-12}$ carboxylic acids is the oxidation of the corresponding aldehydes with molecular oxygen in the liquid phase in the presence or absence of a catalyst or any additives. This general synthesis route is, for example, described in J. Kubitschke et al., "Carboxylic acids, aliphatic" in Ullmann's Encyclopedia of Industrial Chemistry, 2014, Wiley-VCH Verlag GmbH & Co. KGaA, DOI: 10.1002/14356007.a05_235.pub2, chapter 4.2.1 "Aldehyde oxidation" and chapter 7 "Commercially important aliphatic carboxylic acids". The obtained $C_{6-12}$ carboxylic acids are then usually purified by distillation to obtain them in a preferably pure form. However, before they are further processed to their derivatives or used otherwise, they are usually stored in immobile or mobile containers of different size and, if required, transported therein to other locations for their further use. Since most aliphatic carboxylic acids are flammable and corrosive, J. Kubitschke et al. teach in chapter 6 "Storage and transportation" of the above-mentioned article to store and transport them in corrosion-resistant containers. This implies an easy handling in stainless steel or acid-resistant plastic containers without any further specific measures and without taking specific care on the mentioned flammability.

Although J. Kubitschke et al. mentioned the flammability of aliphatic carboxylic acids, an overview on various saturated aliphatic $C_{6-12}$ carboxylic acids based on the data available on the European Chemicals Agency (ECHA) database, which is a publicly available electronic database of chemicals provided by the European Union, revealed typical flash points of 100° C. at ambient pressure such as for example for $C_6$: 104° C. for hexanoic acid;
for $C_7$: 117° C. for heptanoic acid;
for $C_8$: 132° C. for octanoic acid;
118° C. for 2-ethylhexanoic acid;
for $C_9$: 137° C. for nonanoic acid;
117° C. for 3,5,5-trimethylhexanoic acid;
for $C_{10}$: 147° C. for decanoic acid; and
for $C_{12}$: 154° C. for 2-butyloctanoic acid.

Flash points of ≥100° C. are relatively high, but do not per se release from explosion preventing measures such as keeping the aliphatic carboxylic acids under an inert gas atmosphere. N. Allen depicts in his article "Hazards of high flash point liquids in relation to the ATEX 137 directive" in Hazards XXI, Symposium Series No. 155, IChemE 2009, pages 271-276 that liquids with a flash point <40° C. generally require explosion preventing measures, but also liquids with a flash point ≥40° C. may also require such measures if the liquid is intentionally or unintentionally heated above their flash point, mists and aerosols may be formed, chemical reactions or decompositions may occur, or the liquid may be contaminated or mixed with a low flash point component. Since the flash points of saturated aliphatic $C_{6-12}$ carboxylic acids are well above any temperatures that can reasonably be assumed during storage or transport, and also none of the other exceptions mentioned above apply, N. Allen confirms that the storage and transport of saturated aliphatic $C_{6-12}$ carboxylic acids does not require explosion preventing measures such as the provision of an inert gas atmosphere.

Summing up,

- the articles of J. Kubitschke et al. and N. Allen,
- the absence of oxygen sensitive C═C double bonds in saturated aliphatic $C_{6-12}$ carboxylic acids,
- the fact that saturated aliphatic $C_{6-12}$ carboxylic acids are neither explosive nor highly flammable,
- the knowledge that they are generally prepared by oxidation of the respective aldehydes with molecular oxygen, even by using an excess of molecular oxygen, and
- the broad recognition in the literature that carboxylic acids are quite resistant against oxidation, clearly indicate to the person skilled in the art that saturated aliphatic $C_{6-12}$ carboxylic acids can be easily handled, stored and transported under air.

EP application number 20191855.4 deals with the preparation of color stable saturated aliphatic $C_{6-12}$ carboxylic acids, but is silent on how to store or transport them.

However, it was recognized according to the invention that saturated aliphatic $C_{6-12}$ carboxylic acids, even if they have been prepared under the specific color stability enhancing process features described in EP 20191855.4, still tend to degrade over time if stored or transported under conditions described in, or implied by the state of the art.

It was therefore an object of the present invention to improve the storage and transport of saturated aliphatic $C_{6-12}$ carboxylic acids in a way that it does not, or only slightly impair their color stability under thermal stress and/or prevent from, or at least strongly reduce the discoloration of products derived from the stored or transported saturated aliphatic $C_{6-12}$ carboxylic acids, even if they are stored or transported for a long period of time such as for several months. The improved storage and transport shall be easy to perform, preferable in easily available standard containers, and the saturated aliphatic $C_{6-12}$ carboxylic acids shall not be contaminated with detrimental compounds. The object embraces the finding of a process as well as of a container which fulfill the requirements.

We have surprisingly found a container with an inner volume of 0.05 to 10000 $m^3$ containing a) a liquid comprising a saturated aliphatic $C_{6-12}$ carboxylic acid or a mixture thereof, whereas the liquid has a saturated aliphatic $C_{6-12}$ carboxylic acid content of 99 to 100 wt.-% and occupies 1 to 99% of the inner volume of the container, and b) a gas phase above the liquid, in which c) the container is a metallic container, and d) the gas phase above the liquid is an inert gas phase containing nitrogen, helium, neon, argon, krypton, xenon, hydrogen, carbon dioxide, carbon monoxide or a mixture thereof, having a molecular oxygen content of 0 to 100 vol.-ppm.

It was found in EP 20191855.4 that, as soon as even small amounts of molecular oxygen are present, saturated aliphatic $C_{6-12}$ carboxylic acids form under distillation conditions small amounts of components having a high oxidation potential. A deeper investigation on the nature of these high oxidation potential components revealed that they are mainly alkyl hydroperoxides with the general formula (1)

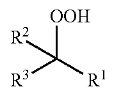

(1)

in which $R^1$ denotes a $C_{1-11}$ radical with a COOH group, $R^2$ denotes a $C_{1-10}$ radical or H, and $R^3$ denotes a $C_{1-5}$ radical or H, whereas the sum of the carbon atoms of $R^1$, $R^2$ and $R^3$ is 5 to 11, depending on the nature of the saturated aliphatic $C_{6-12}$ carboxylic acid. The hydroperoxy group may be located at any carbon atom of the saturated aliphatic $C_{6-12}$ carboxylic acid irrespective of whether the carbon atom is a primary, secondary or tertiary carbon atom, but except for the COOH group. However, tertiary carbon atoms as well as the carbon atom in alpha position to the COOH group are particularly prone for peroxidation.

Components with a high oxidation potential are usually characterized as so-called "active oxygen", which is a quantitative measure of the amount of reactive oxygen. The term "active oxygen" is already known and used in the state of the art, and is for example described in A. Uhl et al., "Peroxy Compounds, Organic" in Ullmann's Encyclopedia of Industrial Chemistry, 2017, Wiley-VCH Verlag GmbH & Co. KGaA, DOI: 10.1002/14356007.a19_199.pub2, chapter 10 "Analytical Determination". The amount of active oxygen of a sample is generally determined by adding a defined amount of an easily oxidable compound, such as salts of iodide(1-) or iron(II), to a defined amount of the sample. The present reactive oxygen oxidizes the oxidable compound and the amount of the oxidized oxidable compound is determined afterwards by titration.

To be more precise regarding the information value of the active oxygen content, its measuring method is explained in more detail. According to the present invention, the determination of active oxygen is preferably performed by oxidation of iodide(1-). This analytical method is called iodometry and is well known by the person skilled in the art. However, it is also roughly explained below.

At the iodometry, a defined amount of an aqueous solution of potassium iodide in acetic acid is added to a defined amount of the sample at room temperature and stirred in order to oxidize the iodide(1-) to elemental iodine. The amount of added potassium iodide relates to the expected amount of active oxygen and can be estimated by preliminary measures. For the iodometric measurement, the amount of the added iodide(1-) has to be a bit higher than the amount oxidized to elemental iodine. The elemental iodine is then titrated with sodium thiosulfate in order to determine the amount of elemental iodine which was formed by the previous oxidation. As an indicator, starch is typically used, which is violet as long as elemental iodine is present and which gets colorless when all the elemental iodine was reduced to iodide. Alternatively, also a platinum electrode can be used. Based on the amount of added potassium iodide and the amount of elemental iodine formed by the oxidation, the amount of the oxidized iodide(1-) can be calculated. According to the formal equation

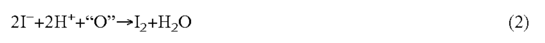

$$2I^-+2H^++\text{“O”}\rightarrow I_2+H_2O \quad (2)$$

and the more detailed equations for alkyl hydroperoxides (3)

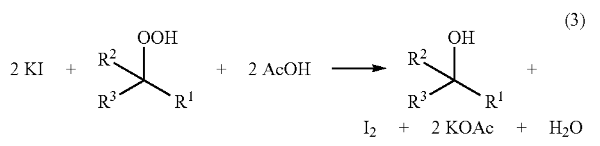

two moles of iodide(1-) react in the presence of acetic acid with one mole of active oxygen atoms. Active oxygen is indicated in formula (2) by "O" and is part of the peroxo group in formula (3). It is reduced to water. In equation (3), "Ac" stands for an acetyl group and the radicals R, $R^1$, $R^2$ and $R^3$ have the meanings as described for formula (1). The active oxygen content of the sample is the weight fraction of the active oxygen atoms based on the weight of the sample and specified in wt.-% or wt.-ppm.

The content of active oxygen can easily be converted into an equivalent content of the peroxide compound, assuming that the active oxygen would solely be bound in the saturated aliphatic $C_{6-12}$ carboxylic acid as hydroperoxide. The conversion can be made by multiplying the determined active oxygen content by the ratio of the molar mass of the hydroperoxy acid to the molar mass of an oxygen atom. In case of 2-ethylhexanoic acid, for example, the multiplication factor is 176.2/16.0=11.0125.

For the sake of completeness, it is also mentioned that the amount of active oxygen in carboxylic acid containing samples can basically also be determined by physical methods such as $^{13}C$-NMR.

However, within the present invention, active oxygen is understood as the mass of oxygen present in the sample which is capable to oxidize iodide(1-) in aqueous acetic acid medium at room temperature and atmospheric pressure to elemental iodine.

It was further found in EP 20191855.4 that active oxygen compounds like alkyl hydroperoxides are able to cause a darkening of the saturated aliphatic carboxylic acids over time during storage, when subjected to thermal stress and/or in products derived therefrom. Regarding the preparation of saturated aliphatic $C_{6-12}$ carboxylic acids by oxidation of the corresponding aldehydes, EP 20191855.4 teaches as a countermeasure against such degradation tendency to remove molecular oxygen from the crude liquid obtained by the oxidation step to a content of ≤10 wt.-ppm before the crude liquid is distilled to isolate the purified saturated aliphatic $C_{6-12}$ carboxylic acid. Such purified saturated aliphatic $C_{6-12}$ carboxylic acids consequently have a very low content of molecular oxygen and a very low content of active oxygen and only show a very low tendency to darken when subjected to thermal stress (i.e. when being heated in the absence of molecular oxygen) and/or in products in which they are regularly applied.

Molecular oxygen and active oxygen are two different types of compounds. Whereas active oxygen is a class of components with a high oxidation potential, as already mentioned above, molecular oxygen is only dissolved $O_2$. Molecular oxygen can be easily measured with molecular oxygen sensitive devices such as optical sensors which are often used in water analysis. As a specific example, an optical fluorescence sensor is mentioned. Optical fluorescence sensors are state of the art and the person skilled in the art knows how to calibrate and to use them. Such sensors are very specific to oxygen and very sensitive to oxygen. They can even measure very low concentrations down to 0.01 wt.-ppm. Since such optical fluorescence sensors are to some extent heat and pressure resistant, they can also be used for in-line measurements.

Molecular oxygen and active oxygen are not only two different types of compounds but can also be measured separately. Molecular oxygen sensitive devices only measure molecular oxygen and not active oxygen and vice versa, active oxygen does not embrace molecular oxygen. Since molecular oxygen reacts only very slowly under the iodometry conditions and furthermore it is good practice to perform the iodometry under inert gas to minimize any interference from molecular oxygen, only active oxygen is measured by iodometry. As advantageous consequence of that, active oxygen and molecular oxygen can be separately determined and evaluated.

Although saturated aliphatic $C_{6-12}$ carboxylic acids are known as stable and non-sensitive compounds which can easily be handled, particularly at atmospheric pressure and ambient temperature, and thus stored and transported under air, it was surprisingly found that, nevertheless, such a treatment causes some degradation which impairs the color stability under thermal stress or causes a discoloration of products derived therefrom. This also applies for the storage and transport of very pure saturated aliphatic $C_{6-12}$ carboxylic acids with only very low contents of molecular oxygen and active oxygen as they may have been obtained by the process described in EP 20191855.4.

It was then surprisingly recognized according to the invention that strict measures which exclude the infiltration of molecular oxygen to the saturated aliphatic $C_{6-12}$ carboxylic acid containing liquid avoid or at least strongly reduce such degradation so that the saturated aliphatic $C_{6-12}$ carboxylic acids handled in such a way are much more color stable at thermal stress and also cause much less discoloration of the products derived therefrom. One effective measure of the present invention is the application of an inert gas atmosphere above the saturated aliphatic $C_{6-12}$ carboxylic acid containing liquid with an at least very low content of molecular oxygen. Another effective measure of the present invention is the prevention of the diffusion of molecular oxygen through the walls of the used container. This can be achieved by using a metallic container.

Thus, the container of the invention is a metallic container with an inner volume of 0.05 to 10000 $m^3$. The mentioned range of the inner volume relates to technically useful amounts. Containers in the sense of the invention can be any vessels, tanks or any other reservoirs in which a liquid comprising a saturated aliphatic $C_{6-12}$ carboxylic acid covered with a gas phase above can be stored or transported.

Metallic means that the walls of the container are either solely made of a metal or at least contain a metallic mantle which may also be part of a composite material. Composite materials can, for example, be containers with coated metals such as painted, varnished, rubberized or enameled metal, metal containers with a non-metallic in-liner such as a synthetic material or plastic containers with a metallic in-liner. Connection holes, as for example the holes for the filling and discharging as well as service holes for pressure balance and the provision of the gas phase, do not count as walls, but shall, of course, also be made of an essentially oxygen diffusion resistant material. Depending on the overall mechanical stability of the walls and the intended use, the container may be mechanically supported by a stable frame or cage. Furthermore, it may also have means for its raising, stacking or fixing.

In case of composite materials in which the metal is not in contact with the saturated aliphatic $C_{6-12}$ carboxylic acid, also non-corrosion resistant metals can be used, provided the material in contact with the corrosive liquid is chemically stable against the corrosive liquid and durably protects the non-corrosion resistant metal from any contact with the corrosive liquid. Under these conditions, even a thin layer of aluminum with a thickness of ≤1 mm or even ≤0.1 mm suffices to prevent the infiltration of molecular oxygen through the wall. In case the metal barrier is not sufficiently resilient for providing the required mechanical stability of the container, which is, for example, the case for a thin layer of aluminum, it has to be mechanically supported. Such a mechanical support may be provided by a mechanically stable wall as part of a composite material and/or by a frame or a cage. In case the metal barrier is made of a non-corrosion resistant metal in a thickness which enables a sufficient mechanical resilience, for example a low alloy steel, it can be protected by a durable corrosion resistant coating, for example by being coated with varnish, rubber or enamel, or by using a corrosion resistant in-liner, as for instance a polyethylene bag or the like.

If the material is in contact with the saturated aliphatic $C_{6-12}$ carboxylic acid containing liquid, it has to be chemically resistant against the corrosive liquid. Such corrosive resistant metals are, for example, zirconium or tantalum, alloys with noble metals such as titanium/palladium, or alloyed steels such as stainless steel. Stainless steel is preferred. Particularly preferred is stainless steel with a PREN value of ≥17. PREN stands for "pitting resistance equivalent number" and is a predictive measurement of a stainless steel's resistance to localized pitting corrosion based on its chemical composition. As a general rule, the higher the PREN value, the more resistant is the stainless steel to localized pitting corrosion. Although such high PREN values are also attained by some ferritic steals such as 1.4113, 1.4526 or 1.4521, whereby the numbers refer to the European standard steel grades, austenitic steels and duplex steels are more preferred, particularly austenitic steels.

Examples of such particularly preferred austenitic steels are 1.4306, 1.4401, 1.4436, 1.4404, 1.4435, 1.4432, 1.4541 and 1.4571.

The inner volume of the container amounts to 0.05 to 10000 $m^3$. This includes mobile containers which can be manually shifted, positioned with forklifts or transported with trucks, rail cars, ships or airplanes, as well as immobile containers in tank farms. Immobile containers, which are also often simply called storage tanks, are typically of a greater size and usually encompass an inner volume of 20 to 10000 $m^3$. They are usually of a cylindrical or spherical shape, whereby cylindrical tanks are typically positioned either upright or horizontally, and may have domed or flat roofs. Mobile containers are characterized by physical dimensions which allow its transportation on ground, water or in the air. Apart from specific ship tanks, which may have containers with an inner volume of 1000 $m^3$ and more, mobile containers typically have an inner volume of 0.05 to 120 $m^3$. As examples of technically notable mobile containers, drums, barrels, IBC tank containers, tank trucks, ISO tank containers, BASF class tank containers and rail tank cars are mentioned. Drums and barrels are generally characterized by an inner volume of 0.05 to 0.25 $m^3$. IBC tank containers (intermediate bulk containers) are reusable, multi-use industrial-grade containers engineered for the handling, transport, and storage of liquids with a typical inner volume of 0.5 to 3 $m^3$ and preferably of around 1 $m^3$. They can easily be moved with forklifts. Tank trucks are generally characterized by an inner volume of 5 to 45 $m^3$, and preferably of 10 to 35 $m^3$. ISO tank containers are based on ISO standards and mounted in a frame. They are designed for the handling, transport, and storage of liquids with a typical inner volume of around 15 to 30 $m^3$ with the advantages of being easily lifted from one standardized transport medium to another and of being stacked on top of each other. A fairly new class of transport containers are BASF class tank containers. They have been developed for a fully automated handling and their transport on automatic guided vehicles, but also enable their transport by trucks, rail cars or ships. Their typical inner volume is in the range of 53 to 73.5 $m^3$. The inner volume of rail tank cars generally range from around 10 to 120 $m^3$.

The term inner volume belongs to the free usable volume inside the container. Possible internals (e.g. for mechanical or fluid-dynamical reasons) as well as connected pipes (e.g. for inlets, outlets or recirculation lines) are not part of the inner volume.

The container of the invention contains a liquid comprising a saturated aliphatic $C_{6-12}$ carboxylic acid or a mixture thereof, and a gas phase above the liquid, whereas $C_{6-12}$ stands for 6 to 12 carbon atoms.

The saturated aliphatic $C_{6-12}$ carboxylic acid can be linear or branched as well as substituted or unsubstituted. Substituted saturated aliphatic $C_{6-12}$ carboxylic acids contain besides carbon and hydrogen one or more heteroatoms, for which halogen is mentioned as an example. Non-substituted saturated aliphatic $C_{6-12}$ carboxylic acids are preferred. Preferred examples broken down by their number of carbon atoms are for $C_6$: hexanoic acid, 2-methylpentanoic acid, 3-methylpentanoic acid, 4-methylpentanoic acid, 2,3-dimethylbutanoic acid and 3,3-dimethylbutanoic acid;

for $C_7$: heptanoic acid and 2-methylhexanoic acid;

for $C_8$: octanoic acid, 2-methylheptanoic acid, 2-ethylhexanoic acid, 2-ethyl-4-methylpentanoic acid and 2-propylpentanoic acid;

for $C_9$: nonanoic acid, 7-methyloctanoic acid and 3,5,5-trimethylhexanoic acid;

for $C_{10}$: decanoic acid, 2-propylheptanoic acid and 2-propyl-4-methylhexanoic acid;

for $C_{11}$: undecanoic acid and 2-methyldecanoic acid; and for $C_{12}$: dodecanoic acid and 2-butyloctanoic acid.

From the above-mentioned list, hexanoic acid, 2-methylpentanoic acid, heptanoic acid, octanoic acid, 2-ethylhexanoic acid, nonanoic acid, 3,5,5-trimethylhexanoic acid, decanoic acid, 2-propylheptanoic acid and dodecanoic acid are more preferred. Particularly preferred are saturated aliphatic $C_{8-12}$ carboxylic acids and within that octanoic acid, 2-ethylhexanoic acid, nonanoic acid, 3,5,5-trimethylhexanoic acid, decanoic acid, 2-propylheptanoic acid and dodecanoic acid. Very particularly preferred is 2-ethylhexanoic acid.

The liquid comprising a saturated aliphatic $C_{6-12}$ carboxylic acid can also be a mixture of different saturated aliphatic $C_{6-12}$ carboxylic acids. As an example of a technically relevant mixture, a mixture containing mainly 3,5,5-trimethylhexanoic acid and other isomeric saturated nonanoic acids is mentioned, which is technically produced and traded as isononanoic acid.

The saturated aliphatic $C_{6-12}$ carboxylic acid containing liquid is characterized by a high content of the saturated aliphatic $C_{6-12}$ carboxylic acid of 99 to 100 wt.-% based on the liquid. In case of a mixture of different saturated aliphatic $C_{6-12}$ carboxylic acids, the mentioned range refers to the mixture. Preferably, the total content of the saturated aliphatic $C_{6-12}$ carboxylic acids is ≥99.3 wt.-%, more preferably ≥99.5 wt.-%, particularly preferably ≥99.8 wt.-% and very particularly preferably ≥99.9 wt.-%.

The saturated aliphatic $C_{6-12}$ carboxylic acids may contain small amounts of impurities and by-products filling the possible gap to 100 wt.-%. Typical impurities and by-products are water, other isomers of the saturated aliphatic $C_{6-12}$ carboxylic acids, including isomers with less carbon atoms, esters of the saturated aliphatic $C_{6-12}$ carboxylic acids with the corresponding or lower chain alcohols, alkyl substituted lactones, or α,β-unsaturated aliphatic $C_{6-12}$ carboxylic acids and their derivatives. The amount and nature of the impurities and by-products generally depend on the nature of the saturated aliphatic $C_{6-12}$ carboxylic acids, particularly whether they are linear or branched, their production process and their purification procedure. To support the efforts of retaining a low degradation tendency during the storage and transport of the container, the liquid preferably has an active oxygen content of 0 to 100 wt.-ppm, more preferably of ≤50 wt.-ppm and particularly preferably of ≤10 wt.-ppm. It typically has an active oxygen content of ≥1 wt.-ppm. In addition to that, it is advantageous that the liquid also has a low content of molecular oxygen dissolved therein, whereby a range of 0 to 10 wt.-ppm is preferred. More preferably, the liquid contains ≤5 wt.-ppm and particularly preferably ≤2 wt.-ppm of molecular oxygen.

Due to the generally low melting points of most of the saturated aliphatic $C_{6-12}$ carboxylic acids, and particularly of the branched ones, most of them are already present as a liquid at ambient temperatures. However, some linear ones have melting points even above 0° C., as can be seen in the below list of the melting points of some saturated aliphatic $C_{6-12}$ carboxylic acids.

−70° C.: 3,5,5-trimethylhexanoic acid

−59° C.: 2-ethylhexanoic acid

−10° C.: heptanoic acid

−4° C.: hexanoic acid 12 to 15° C.: nonanoic acid

17° C.: octanoic acid

31° C.: decanoic acid

44° C.: dodecanoic acid

Depending on the expected temperature conditions during storage and transport, which may possibly be in the range of 20±30° C., depending on the location and season, the container can be isolated or heated with a trace heating, if required, to keep the saturated aliphatic $C_{6-12}$ carboxylic acid liquid.

The container of the invention allows a very broad range of filling levels so that the filling degree may vary from only 1 to 99% based on the inner volume of the container. Particularly the above-mentioned strict measures regarding the existence of an inert gas atmosphere with a very low content of molecular oxygen and use of metallic containers preventing the diffusion of molecular oxygen through the walls, enable this high flexibility in the filling degree. Such a great flexibility is particularly advantageous for containers in which the saturated aliphatic $C_{6-12}$ carboxylic acids are gradually withdrawn over a longer period of time, or for storage tanks in which the saturated aliphatic $C_{6-12}$ carboxylic acids are irregularly withdrawn and replenished. Nevertheless, in case of a mere storage or a transport, it is generally advantageous to apply a higher filling level. In a preferred embodiment, the liquid occupies 90 to 99% of the inner volume of the container, more preferably ≥95% and particularly preferably ≥98%.

Beside the use of a metallic container, which prevents the diffusion of molecular oxygen through the walls, the other effective measure of the present invention is the application of an inert gas phase above the liquid. The term inert means chemically inert against the respective saturated aliphatic $C_{6-12}$ carboxylic acid. The inert gas phase contains nitrogen ($N_2$), helium (He), neon (Ne), argon (Ar), krypton (Kr), xenon (Xe), hydrogen ($H_2$), carbon dioxide ($CO_2$), carbon monoxide (CO) or a mixture thereof and is characterized by a molecular oxygen content of 0 to 100 vol.-ppm. Preferably, it contains nitrogen, helium, neon, argon, krypton, xenon, carbon dioxide or a mixture thereof. In addition to the above-mentioned inert components, the inert gas phase also contains a low amount of the saturated aliphatic $C_{6-12}$ carboxylic acid or acids of the liquid which have been vaporized according to their vapor pressure. Their concentration in the gas phase strongly depends on the nature of the saturated aliphatic $C_{6-12}$ carboxylic acid and the existing temperature. However, even for the saturated aliphatic $C_{6-12}$ carboxylic acid with the highest vapor pressure and a temperature of 50° C., its concentration in the gas phase is well below 0.4 vol.-%.

As a general rule, the lower the content of molecular oxygen in the gas phase, the better the prevention against the degradation of the saturated aliphatic $C_{6-12}$ carboxylic acid in the liquid. Therefore, the molecular oxygen content in the inert gas phase is preferably ≤50 vol.-ppm, more preferably ≤20 vol.-ppm, particularly preferably ≤10 vol.-ppm, very particularly preferably ≤5 vol.-ppm and especially ≤2 vol.-ppm. Beside small amounts of molecular oxygen, the inert gas phase may also contain small amounts of the typical impurities of the respective gases such as water vapor, lower hydrocarbons, or noble gases in case of nitrogen, and in case of carbon dioxide also traces of carbon monoxide. Depending on the applied purity of the mentioned inert gases, the inert gas phase preferably contains ≥99.5 vol.-%, more preferably ≥99.8 vol.-%, particularly preferably ≥99.9 vol.-% and very particularly preferably ≥99.99 vol.-% of these gases, calculated on a basis, in which the vapor of the saturated aliphatic $C_{6-12}$ carboxylic acids vaporized from the liquid was deducted and the remaining gas phase set to 100 vol.-%. The plural "acids" also embraces the singular "acid" in case the liquid contains only one saturated aliphatic $C_{6-12}$ carboxylic acid. This deduction enables the provision of a percentage value for the purity of the inert gas which is independent from the nature of the saturated aliphatic $C_{6-12}$ carboxylic acid as well as from the temperature of the container.

Due to the good availability of nitrogen as a technical standard inert gas, nitrogen is preferred. In a particularly preferred embodiment, the inert gas phase contains 99.9 vol.-% nitrogen, calculated on a basis, in which the vapor of the saturated aliphatic $C_{6-12}$ carboxylic acids vaporized from the liquid was deducted and the remaining gas phase set to 100 vol.-%.

A possible alternative to the inventive provision of an inert gas phase above the saturated aliphatic $C_{6-12}$ carboxylic acid containing liquid is the absence of a gas phase. Since the liquid would then be totally encircled by metal containing walls, at least one wall has to be flexible or mobile to compensate thermal expansions and contractions, and to enable filling and discharging. Such capability is provided by so-called floating roof tanks in which the upper cover floats on the liquid filling. In order to prevent the upper cover from weather, the floating roof tank may additionally have a fixed top at the upper end. Such tanks are called internal floating roof tanks and may, as the case may be, contain an inert gas atmosphere in the inner space between the floating roof and the fixed top.

Since the container of the invention is typically intended to store and transport saturated aliphatic $C_{6-12}$ carboxylic acids, it is typically handled at a temperature of 20±30° C., or even at −30 to +50° C., depending on the location and season. As already mentioned above, the container may be thermally isolated or heated if required, i.e. if the respective liquid has a melting point below the expected ambient temperature. The temperature of the liquid is preferably kept at ≥−20° C., more preferably at ≥−10° C., particularly preferably at ≥0° C., and preferably at ≤40° C. and more preferably at ≤35° C.

Regarding the pressure, the inert gas phase may be kept in a range of 0.09 to 0.6 MPa abs which relates to a very small underpressure up to a low excess pressure. Since even a very small underpressure may cause some infiltration of the surrounding air if the caps or seals would not be absolutely tight, it is preferred to at least apply a pressure substantially equal to, or slightly above the surrounding atmospheric pressure, i.e. at ≥0.1 MPa abs, preferably at ≥0.102 MPa abs. On the other hand, the higher the excess pressure the more complex the filling and the higher the risk of unwanted instances. Thus, it is preferred to only apply a low excess pressure resulting in a total pressure of ≤0.2 MPa abs, more preferably of ≤0.15 MPa abs, particularly preferably of ≤0.12 MPa abs and very particularly preferably of ≤0.11 MPa abs.

A further aspect of the invention is a process for the storage and transport of a liquid comprising a saturated aliphatic $C_{6-12}$ carboxylic acid or a mixture thereof was surprisingly found, whereas the liquid has a saturated aliphatic $C_{6-12}$ carboxylic acid content of 99 to 100 wt.-%, by filling the liquid into a container with an inner volume of 0.05 to 10000 $m^3$ in an amount that the liquid occupies 1 to 99% of the inner volume of the container, wherein the liquid is kept therein for more than 1 hour, and in which a) the container is a metallic container, and b) the gas phase in the container is inertized with an inert gas containing nitrogen, helium, neon, argon, krypton, xenon, hydrogen, carbon dioxide, carbon monoxide or a mixture thereof, having a molecular oxygen content of 0 to 100 vol.-ppm.

The explanations and preferences of the terms, expressions, lists and values which have already been used and explained above in connection with the description of the container, also apply correspondingly to the terms, expressions, lists and values of the process. In case of discrepancies, the explanations and preferences explicitly disclosed with regard to the process shall prevail for the process.

In the process of the invention, the liquid comprising the saturated aliphatic $C_{6-12}$ carboxylic acid or a mixture thereof is filled into a metallic container in an amount occupying 1 to 99% of the inner volume of the container. As already mentioned above in connection with the description of the container, the container has an inner volume of 0.05 to 10000 $m^3$ and can be a mobile or immobile container with walls either solely made of a metal or at least containing a metallic mantle, which may also be part of a composite material. Although it would be possible to first fill the liquid into a non-inertized container, e.g. which contains a gas phase with a molecular oxygen content>100 vol.-ppm, it is advantageous if the gas phase of the container is already inertized with an inert gas containing nitrogen, helium, neon, argon, krypton, xenon, hydrogen, carbon dioxide, carbon monoxide or a mixture thereof and having a molecular oxygen content of 0 to 100 vol.-ppm, preferably ≤50 vol.-ppm, more preferably ≤20 vol.-ppm, particularly preferably ≤10 vol.-ppm, very particularly preferably ≤5 vol.-ppm and especially ≤2 vol.-ppm. This does also apply for the equipment required for the filling which is in direct contact with the liquid, such as pipes, valves or fittings. In the event that the container would contain during the filling procedure a gas phase with a molecular oxygen content above the intended value, the gas phase is at least afterwards exchanged or at least modified with an inert gas to adjust the intended inert gas quality.

As already mentioned in connection with the description of the container, a higher filling level is advantageous due a smaller gaseous reservoir above the liquid. In a preferred process, the liquid occupies 90 to 99% of the inner volume of the container, more preferably ≥95% and particularly preferably ≥98%.

The container to be filled with the liquid may already contain some liquid, which is, for example, usual for storage tanks in tank farms, or it may be empty or nearly empty, which may, for instance, be routine for transport container which are circulated between the filling station and the discharging station.

If the connections have to be capped after the filling, which is the case for mobile containers before transporting them, it has to be ensured that the inert gas phase above the liquid keeps the intended quality.

The filled container can then be kept for storage or transported. Storage means the keeping of the container at the same place, whereas transport means the movement of the container to another place. For the sake of completeness, it is mentioned that also mobile container can be used for storage, which is the case if they are kept at a fixed place, for example before or after its transport or generally. Transport can take place on ground, on water or in the air.

The process of the invention is preferably performed by using a mobile container with an inner volume of 0.05 to 120 $m^3$. Such mobile containers enable a high flexibility for storing and transporting the saturated aliphatic $C_{6-12}$ carboxylic acid. Technically notable mobile containers of that size are, for example, drums, barrels, IBC tank containers, truck tanks, ISO tank containers, BASF class tank containers or rail tank cars.

The inert gas phase in the container is usually kept at a pressure in the range of 0.09 to 0.6 MPa abs, preferably at ≥0.102 MPa abs and preferably at ≤0.2 MPa abs, and typically handied at a temperature of 20±30° C., or even at −30 to +50° C., depending on the location and season, whereas the preferences already mentioned in connection with the description of the container apply accordingly. The containers may be thermally isolated or heated if required.

Once the liquid comprising the saturated aliphatic $C_{6-12}$ carboxylic acid is filled in, it is kept under the inert conditions for more than 1 hour, preferably for ≥1 day, more preferably for ≥1 week and particularly preferably for ≥4 weeks. There are no restrictions for an upper time limit. Even if the liquid is stored for one year or longer under the conditions of the invention, its degradation would be measurably lower than if it would have been stored in an oxygen permeable container and/or under a gas phase with a considerable content of molecular oxygen.

Nevertheless and in addition to the use of an oxygen-impermeable metallic container and the provision of an inert gas phase above the liquid, it is additionally advantageous for preventing the degradation of the saturated aliphatic $C_{6-12}$ carboxylic acid if the liquid already has a low content of molecular oxygen dissolved therein, whereby a range of 0 to 10 wt.-ppm of molecular oxygen is preferred, ≤5 wt.-ppm are more preferred and ≤2 wt.-ppm are particularly preferred.

Furthermore and to support the efforts of retaining a low degradation tendency during the storage and transport of the container, the liquid preferably has an active oxygen content of 0 to 100 wt.-ppm, more preferably of ≤50 wt.-ppm and particularly preferably of ≤10 wt.-ppm, and preferably ≥1 wt.-ppm.

Analogous to the filling of the container, also the discharging of the saturated aliphatic $C_{6-12}$ carboxylic acid containing liquid is advantageously performed by avoiding the direct contact of the liquid with an oxygen-containing gas phase having an oxygen content of >100 vol.-ppm. Consequently, the equipment required for the discharging which is in direct contact with the liquid, such as pipes, valves or fittings, should preferably be inertized.

Moreover, and as also already mentioned in connection with the description of the container, nitrogen is preferred as inert gas, due to its good availability as a technical standard inert gas. In a particularly preferred process, the inert gas phase contains ≥99.9 vol.-% nitrogen.

As saturated aliphatic $C_{6-12}$ carboxylic acids, hexanoic acid, 2-methylpentanoic acid, heptanoic acid, octanoic acid, 2-ethylhexanoic acid, nonanoic acid, 3,5,5-trimethylhexanoic acid, decanoic acid, 2-propylheptanoic acid and dodecanoic acid are more preferred. Particularly preferred are saturated aliphatic $C_{8-12}$ carboxylic acids and within that octanoic acid, 2-ethylhexanoic acid, nonanoic acid, 3,5,5-trimethylhexanoic acid, decanoic acid, 2-propylheptanoic acid and dodecanoic acid. Very particularly preferred is 2-ethylhexanoic acid.

A further aspect of the invention is the use of nitrogen as an inertizing gas for providing an inertized gas phase with a molecular oxygen content of 0 to 100 vol.-ppm in a metallic container with an inner volume of 0.05 to 10000 $m^3$ in which a liquid comprising a saturated aliphatic $C_{6-12}$ carboxylic acid or a mixture thereof having a content of the saturated aliphatic $C_{6-12}$ carboxylic acid of 99 to 100 wt.-% occupies 1 to 99% of the inner volume of the container, is stored or transported for more than 1 hour.

In a general embodiment, 2-ethylhexanoic acid is filled in a 1 $m^3$ metallic IBC tank container, which was previously inertized with nitrogen having a molecular oxygen content of ≤5 vol.-ppm, in an amount occupying 98% of the inner volume. The container is tightly closed at a nitrogen gas pressure of 0.1 to 0.11 MPa abs and then stored and/or transported.

In another general embodiment, a mixture of 3,5,5-trimethylhexanoic acid and other saturated aliphatic branched $C_9$ carboxylic acids is filled in a 26 $m^3$ ISO tank container, which was previously inertized with nitrogen having a molecular oxygen content of 10 vol.-ppm, in an amount occupying 95% of the inner volume. The container is tightly closed at a nitrogen gas pressure of 0.1 to 0.15 MPa abs and then transported with a truck, a rail car and/or a container ship.

A further general embodiment relates to the storage of 2-ethylhexanoic acid in a tank farm. 2-Ethylhexanoic acid, which is continuously produced and purified in a production plant, is continuously pumped through a completely filled pipeline to an immobile 2000 $m^3$ tank in a tank farm. The tank contains an inertized gas phase with a nitrogen content of ≥99.9 vol.-% and a molecular oxygen content of ≤5 wt.-ppm. Depending on the use and demand of the stored 2-ethylhexanoic acid, it is either continuously or irregularly discharged. Consequently, the filling level may vary and be in the range of 1 to 99%, depending on the supplied and discharged amounts of 2-ethylhexanoic acid.

The container as well as the process of the invention enable the storage and transport of saturated aliphatic $C_{6-12}$ carboxylic acids in a way that it does not, or only slightly impair their color stability under thermal stress and/or prevent from, or at least strongly reduce the discoloration of products derived from the stored or transported saturated aliphatic $C_{6-12}$ carboxylic acids, even if they are stored or transported for a long period of time such as for several months. The improved storage and transport can be easily performed in available standard containers without contaminating the saturated aliphatic $C_{6-12}$ carboxylic acids with detrimental compounds.

EXAMPLES

Determination of Active Oxygen by Iodometry

The content of active oxygen in 2-ethylhexanoic acid was determined by iodometry. The following gives a general description on how the determination was performed.

Approximately 5 g of the sample, weighed to the nearest 0.1 mg, are placed in a reaction vial, flushed with argon, and 40 ml of a 1:1 acetic acid/chloroform mixture added to dissolve the sample. The reaction vial is provided with a cooler and placed in a stirring heating block, that is already preheated to 80° C. A weak argon flow is passed through the cooler to prevent the ingress of air. After the temperature has equilibrated, 5.0 mL of a saturated potassium iodide solution (ca. 60.0 g potassium iodide dissolved in 100 mL deionized water) are added through the cooler and the mixture is boiled under reflux for 10 min. In the next step, 40.0 mL deionized water are added, and the sample solution is titrated with a 0.01 M thiosulfate solution while using a platinum electrode as end point indicator.

Determination of Molecular Oxygen

The content of molecular oxygen in 2-ethylhexanoic acid was determined by a high precision and highly $O_2$ sensitive optical fluorescence sensor, which was suitable to measure molecular oxygen in carboxylic acids. In the examples, an optical sensor named FDO® 925 from WTW was used.

The measured data were cross-checked by additional measurements using a galvanic cell oxygen analyzer, which is also known as a Hersch cell.

Determination of the APHA Color Number

The APHA color number of the samples was determined by a colorimeter which was in advance calibrated against distilled water. In the examples, a colorimeter named Lico® 620 from Hach with a 10 mL cuvette was used.

Description of the Esterification Test

A 4 liter stirred tank reactor was filled under nitrogen (molecular oxygen content≤100 ppm) with 520 g (5 mol) of neopentyl glycol and 1469 g (10.2 mol) of 2-ethylhexanoic acid and 0.75 g of powdered tin oxide as catalyst. The mixture is then heated to 180-190° C. under ambient pressure to form the diester between neopentyl glycol and 2-ethylhexanoic acid, and the formed water allowed to distill off. The reaction is finished when no more water is formed. The mixture is then cooled to approximately 60° C., a defined amount of active charcoal added and kept for 30 minutes under stirring. The suspension was then filtered and the APHA color number determined.

Example 1 (Comparative)

2-Ethylhexanoic acid was produced in a technical plant with a production capacity of around 3.75 tons 2-ethylhexanoic acid per hour by continuously oxidizing 2-ethylhexanal with pure oxygen at a temperature of 30 to 60° C. and a pressure of 0.25 MPa abs and in the presence of 0.4 wt.-% of potassium ions in the reaction mixture. The technical plant contained three reactors connected in series and the addition of the oxygen feed was divided between these three reactors. The 2-ethylhexanal and the potassium salt were added to the first reactor. The obtained crude 2-ethylhexanoic acid was stripped with a stream of nitrogen (molecular oxygen content≤100 ppm) until the content of the dissolved molecular oxygen was only 2 wt.-ppm, subsequently distilled in a distillation column and purified 2-ethylhexanoic acid withdrawn as a side stream. The purified 2-ethylhexanoic acid had a 2-ethylhexanoic acid content of 99.85 wt.-%, analyzed by gas chromatography, contained 2 wt.-ppm active oxygen, <1 wt.-ppm dissolved molecular oxygen and showed an APHA color number of 0.

The purified liquid 2-ethylhexanoic acid was then filled in a non-inertized, air containing 1 $m^3$ polyethylene IBC-container in an amount occupying around 95% of the inner volume. The IBC-container was then closed tightly and stored and transported for around three weeks at a pressure of 0.12 MPa abs and a temperature in the range of 0 to 40° C.

After storage and transport, samples of the 2-ethylhexanoic acid have been taken under an inert nitrogen atmosphere and esterified as described by the esterification test to determine the amount of active charcoal required for attaining an APHA color number of <10. The required amount of active charcoal was 8.4 g per kg of the applied educts (neopentyl glycol plus 2-ethylhexanoic acid).

Example 2 (According to the Invention)

2-Ethylhexanoic acid was produced in the same technical plant and under the same conditions as described in example 1. It had a 2-ethylhexanoic acid content of 99.85 wt.-%, analyzed by gas chromatography, contained 2 wt.-ppm active oxygen, <1 wt.-ppm dissolved molecular oxygen and showed an APHA color number of 0.

The purified liquid 2-ethylhexanoic acid was then filled in a 1 $m^3$ nitrogen inertized (molecular oxygen content≤100 vol.-ppm) stainless steel IBC-container in an amount occupying around 95% of the inner volume. The IBC-container was then closed tightly and stored and transported for around three weeks at a pressure of 0.12 MPa abs and a temperature in the range of 0 to 40° C.

After storage and transport, samples of the 2-ethylhexanoic acid have been taken under an inert nitrogen atmosphere and esterified as described by the esterification test to determine the amount of active charcoal required for attaining an APHA color number of <10. The required amount of active charcoal was only 1.4 g per kg of the applied educts (neopentyl glycol plus 2-ethylhexanoic acid).

Examples 1 and 2 are identical in the production and nature of the purified 2-ethylhexanoic acid, in the storage and transport period, in the applied pressure and temperature, as well as in the performance of the esterification test, and only differ in the material of the container used for storage and transport and in the nature of the gas atmosphere above the 2-ethylhexanoic acid. Whereas in example 1, the 2-ethylhexanoic acid was stored and transported in a typical polyethylene container under an atmosphere of air (0.12 MPa abs), the 2-ethylhexanoic acid in example 2 was stored and transported in an oxygen-impermeable stainless steel container under an atmosphere of nitrogen inert gas (0.12 MPa abs). These two differences result in a very strong decrease of the amount of active charcoal required for decolorizing the diester formed in the esterification test to an APHA color number of <10 by a factor of 6 between 8.4 g per kg of the applied educts in example 1 and 1.4 g in example 2.

The inventive measures as applied in example 2 prevent, or at least strongly reduce the oxygen induced degradation of the 2-ethylhexanoic acid during storage and transport and thus prevent from, or at least strongly reduce the discoloration of the products derived therefrom.

The invention claimed is:

1. A process for the storage and transport of a liquid comprising a non-substituted saturated aliphatic $C_{6-12}$ carboxylic acid or a mixture thereof, whereas the liquid has a non-substituted saturated aliphatic $C_{6-12}$ carboxylic acid content of 99 to 100 wt.-%, by filling the liquid into a container with an inner volume of 0.05 to 10000 $m^3$ in an amount that the liquid occupies 1 to 99% of the inner volume of the container and having a gas phase above, wherein the liquid is kept therein for more than 1 hour, characterized in that:

a) the container is a metallic container comprising walls wherein the walls are solely made of metal, wherein the metal being in contact with the non-substituted saturated aliphatic $C_{6-12}$ carboxlic acid is selected from the group consisting of zirconium, tantalum, an alloy with noble metals and alloyed steel, or comprise a composite material comprising metal sufficient to prevent infiltration of molecular oxygen through the walls, and b) the gas phase in the container is inertized with an inert gas containing nitrogen, helium, neon, argon, krypton, xenon, hydrogen, carbon dioxide, carbon monoxide or a mixture thereof, having a molecular oxygen content of 0 to 100 vol.-ppm.

2. The process of claim 1, wherein the container is a mobile container with an inner volume of 0.05 to 120 $m^3$.

3. The process of claim 1, wherein the liquid is kept therein for ≥1 week.

4. The process of claim 1, wherein the liquid has an active oxygen content of 0 to 100 wt.-ppm.

5. The process of claim 1, wherein the gas phase contains >99.9 vol.-% nitrogen.

6. The process of claim 1, wherein the non-substituted saturated aliphatic $C_{6-12}$ carboxylic acid is 2-ethylhexanoic acid.

7. The process of claim 1, wherein the walls of the metallic container are solely made of metal.

8. The process of claim 1, wherein the walls of the metallic container comprise a composite material comprising metal sufficient to prevent infiltration of molecular oxygen through the wall.

9. The process of claim 1, wherein the alloy with noble metals is a titanium/palladium alloy.

10. The process of claim 1, wherein the alloyed steel is stainless steel.

11. The process of claim 10, wherein the stainless steel has a pitting resistance equivalent number PREN of ≥17.

12. The process of claim 1, wherein the walls of the metallic container comprise a composite material containing a metal being painted, varnished, rubberized or enameled, or a non-metallic in-liner with a metallic in-liner.

13. The process of claim 12, wherein the metal is aluminum.

* * * * *